United States Patent
Davis et al.

(10) Patent No.: US 6,281,405 B1
(45) Date of Patent: Aug. 28, 2001

(54) ALKYLATION PROCESS USING MEMBRANE FOR RECOVERY OF HALIDES

(75) Inventors: Mark M. Davis, Chicago, IL (US); William B. Dolan, Yardley, PA (US); Robert J. Schmidt, Barrington; Paul J. Kuchar, Decatur, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/731,105

(22) Filed: Dec. 6, 2000

Related U.S. Application Data

(62) Division of application No. 09/343,496, filed on Jun. 30, 1999.

(51) Int. Cl.[7] .................................................. C07C 7/144
(52) U.S. Cl. ........................ 585/719; 585/709; 585/712; 585/713; 585/723; 585/818; 208/262.1
(58) Field of Search ..................... 585/818, 709, 585/712, 713, 723, 719; 208/262.1

(56) References Cited

U.S. PATENT DOCUMENTS

| | | | |
|---|---|---|---|
| 4,929,794 | 5/1990 | Schmidt et al. | 585/737 |
| 4,971,695 | 11/1990 | Kawakami et al. | 210/500 |
| 5,026,950 | 6/1991 | Schmidt et al. | 585/737 |
| 5,489,732 | 2/1996 | Zhang et al. | 585/467 |

OTHER PUBLICATIONS

Cusher, Nelson A. UOP Butamer Process (Chapters 9.2 and 9.3), *Handbook of Petroleum Refining Processes*, 2nd Ed., edited by Robert A. Meyers (McGraw–Hill, New York, 1997).

Baker, Richard W. *Membrane Technology, Kirk–Othmer Encyclopedia of Chemical Technology*,. (John Wiley, New York, 1995) 4th Ed vol. 16 pp. 135–193.

Hsieh, H.P. *Inorganic Membranes for Separation and Reaction, Membrane Science and Technology Series 3*, (Elsevier Science B. V., New York, 1996) pp. 1–13.

*Membrane Separation Processes*, edited by P. Meares, (Elsevier Scientific, New York, 1976) pp. 308–326.

Pan, C. Y. and Habgood, H. W. An Analysis of the Single–Stage Gaseous Permeation Process, *Ind. Eng. Chem., Fundamen.*, vol. 13, No. 4, 1974, pp. 323–331.

Pan, C. Y. and Habgood, H. W. Gas Separation by Permeation, Part 1: Calculation Methods and Parametric Analysis *The Canadian Journal of Chemical Engineering.*, vol. 56, Apr. 1978, pp. 197–209.

Pan, C. Y. and Habgood, H. W . . . Gas Separation by Permeation, Part II: Effect of Permeate Pressure Drop and Choice of Permeate Pressure *The Canadian Journal of Chemical Engineering.*, vol. 56, Apr. 1978, pp. 210–217.

Cooley, T.E. and Dethloff, W.L. *Pollution Control: Field Tests Show Membrane Processing Attractive*, *CEP*, Oct. 1985, pp. 45–50.

*Primary Examiner*—Walter D. Griffin
*Assistant Examiner*—Tam M. Nguyen
(74) *Attorney, Agent, or Firm*—John G. Tolomei; John F. Spears, Jr.; Michael A. Moore

(57) ABSTRACT

A process for recovering halides from hydrocarbon containing streams is disclosed using a sulfonated hexafluro bis-A-polysulfone membrane of polymers and copolymers having the polymer repeat unit of the formula:

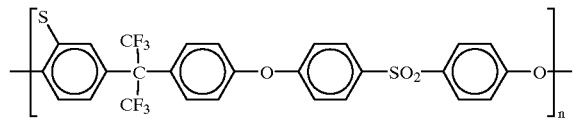

in the polymer or copolymer. This process is applicable to recovering and recycling hydrogen chloride, which is used as a catalytic promoter, in hydrocarbon conversion processes such as isomerization and alkylation.

7 Claims, 3 Drawing Sheets

ALKYLATION PROCESS USING MEMBRANE FOR RECOVERY OF HALIDES

CROSS-REFERENCE TO RELATED APPLICATION

This application is a division of U.S. application Ser. No. 09/343,496 filed Jun. 30, 1999, the entire contents of which are hereby incorporated by reference.

FIELD OF THE INVENTION

This invention relates to a process for the recovery of halides from streams containing light hydrocarbons.

BACKGROUND OF THE INVENTION

Numerous hydrocarbon conversion processes are widely used to alter the structure or properties of hydrocarbon streams. For example, isomerization processes rearrange the molecular structure from straight chain paraffinic hydrocarbons to more highly branched hydrocarbons that generally have a higher octane rating or increased utility as substrates for other conversion processes. Alkylation processes alkylate hydrocarbon alkylation substrates, such as aromatics or paraffins, with hydrocarbon alkylating agents, such as olefins, to produce motor fuels and useful industrial chemicals such as ethylbenzene, cumene, and linear alkyl benzenes that are used to make detergents. Additional processes include dehydrogenation, transalkylation, reforming, and others. Operating conditions and methods for carrying out these processes are well known by those skilled in the art.

Many of these processes share the common feature of using a catalyst in the presence of one or more materials that enhance the effectiveness of the catalyst in the reaction zone. These performance enhancing materials can operate in many ways, such as increasing or attenuating catalyst activity, neutralizing catalyst poisons, or solubilizing catalyst or feed contaminants. Such performance enhancement materials may be chemically or physically sorbed on the catalyst or dispersed in the hydrocarbon stream.

Where the hydrocarbon product stream leaving a hydrocarbon conversion zone contains the performance enhancing material or beneficent material, methods are sought for preventing contamination of the hydrocarbon product with the beneficent material and the loss of this beneficent material to the product stream. For example, many isomerization processes employ a highly effective platinum on chlorided alumina catalyst system in the reaction zone. The chlorided catalyst requires a continual addition of chloride to replace chloride lost from the surface of the catalyst in to the product stream. Hydrogen chloride and/or volatile organic chlorides escape from the process via a stabilizer overhead stream and, apart form the loss of chloride, pose environmental concern. In addition to the loss of chlorides and environmental concerns, chloride loss hinders the operation of chloride promoted isomerization zones in other ways. For example, the recycle of hydrogen or hydrocarbons through a zeolitic adsorption bed or a zeolitic conversion zone is not practical when a chloride type catalyst is used in the isomerization reaction zone, unless hydrogen chloride is removed from the recycle stream. Hydrogen chloride that is produced by the addition of chloride to the isomerization zone or that is released from the isomerization catalyst results in significant amounts of hydrogen chloride leaving in the effluent from the isomerization zone. Contact of this hydrogen chloride with a zeolite in, say, an adsorption bed or in a catalytic conversion zone, particularly in the presence of moisture and high temperature, will decompose the matrix structure of many zeolites, thereby destroying any adsorptive or catalytic function. Therefore, absent chloride neutralization methods, chlorided catalyst systems generally have insufficient compatibility with many zeolitic adsorbents or catalysts to permit simultaneous use.

Alkylation of hydrocarbons presents another case where contamination by a performance enhancement material can pose concern. Alkylation processes can use a solid chlorided alumina catalyst in the alkylation reactor, with the chloride acting as a performance enhancement material for the catalyst. In the course of alkylation, some chloride is lost from the catalyst into the product stream. In addition, the current commercial versions of these solid alkylation catalysts tend to experience fairly rapidly deactivation, which necessitates frequent regeneration, which in turn usually leads to the loss of more chloride from the catalyst into one or more regeneration effluent streams. Unless some or most of the lost chloride in the product stream and the regeneration effluent stream(s) is recovered and returned to the catalyst, the costs of neutralizing chlorides and of supplying fresh or make-up chloride to the catalyst can render alkylation processes that use solid chlorided catalysts less economical. Thus, methods have been sought for recovering and recycling materials, such as hydrogen chloride, which act to enhance or benefit the performance of catalysts in conversion zones when such materials are carried from the conversion zone by a hydrocarbon-containing effluent stream.

Since the 1960s, the chemical and petrochemical industries are increasingly using membranes in a broad variety of separation and recovery applications. A membrane is a thin barrier having two sides and separating two fluids. In a membrane process, a feed stream passes to one side of the membrane, which is commonly called the feed side or nonpermeate side of the membrane. The feed stream contains a permeable component and a nonpermeable component, which is used herein to refer to a component that has a permeance that is less than that of the permeable component. The permeable component selectively passes through the membrane and is recovered on the reverse side, or permeate side, of the membrane in a stream which is called the permeate. The portion of the feed stream that does not selectively pass through the membrane, including the nonpermeable component, is recovered from the nonpermeate side of the membrane in a stream which is called the nonpermeate and which is also commonly referred to as the concentrate, the retentate, or the residue. General information on membrane separation processes can be found in Perry's Chemical Engineers' Handbook, Sixth Edition, edited by R. H. Perry and D. W. Green, published by McGraw-Hill Book Company, New York, in 1984.

In order for the permeable component to permeate from the nonpermeate side to the permeate side of the membrane at a particular location of a membrane, the local partial pressure of the permeable component at that particular location at or near the surface of the membrane must be greater on the nonpermeate side of the membrane than on the permeate side of the membrane. Local partial pressure of the permeable component means the product of the mole fraction of the permeable component and the total pressure, both determined locally at a given particular point at or near the surface of the membrane. In practice, the local mole fraction and local total pressure cannot be measured precisely at the surface of the membrane. Rather, the local mole fraction and total pressure are determined at least in part by the bulk flow rates, compositions, and pressures of the stream that are contacted with the membrane, and by controlling these streams, suitable local partial pressures of the permeable component can be controlled on both sides of the membrane.

The separation of gas streams using dense membranes that are nonporous and yet permeable is well known. Dense membranes consist of a dense film through which a pressure and concentration gradient will force the diffusion of certain components. The relative rates of transport of various components through the dense film does not necessarily depend on the size of the components, as much as it depends on the diffusivity and solubility of the components. See the article entitled "Membrane Technology," written by Richard W. Baker, appearing at pp. 135–193 in Vol. 16 of the *Kirk-Othmer Encyclopedia of Chemical Technology*, 4$^{th}$ Edition, published by John Wiley, in New York, in 1995.

Two of the chief criteria for a dense membrane separation process are permeance and selectivity. At this point, it is useful for the sake of clarity to define these terms:

i. Permeance

In simple permeation, the permeation flux of a species i across a membrane may be expressed by the formula, $$R_i = P_i * (y_H * H - y_L * L)$$

where $R_i$ equals the rate of permeation in units of standard volume of species i per unit of time per unit of membrane cross-sectional area, $P_i$ equals the permeance, $y_H$ equals the mole fraction of species i on the high-pressure or nonpermeate side of the membrane, H equals the pressure on the high-pressure side of the membrane, $y_L$ equals the mole fraction of species i on the low-pressure or permeate side of the membrane, and L equals the pressure on the low-pressure side of the membrane. Thus, permeance has units of standard volume of species i per unit of time per unit of membrane cross-sectional area per unit of pressure.

ii. Selectivity

Selectivity is defined as the ratio of the permeance of species i relative to the permeance of another species j and can be expressed by the equation, $$S_{ij} = P_i/P_j$$

In this equation, the convention is to put the numerically larger permeance in the numerator and the numerically smaller permeance in the denominator, so that the higher the selectivity of a membrane, the more desirable is the use of that membrane in a process for separating species i and j.

Examples of dense membranes include sulfonated fluorinated polysulfone membranes that comprise polymers, including copolymers, which have the polymer repeat unit of the following general type of structure in the polymer or copolymer, which is hereinafter referred to as formula (I):

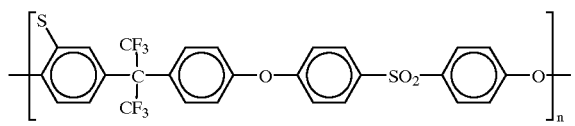

In the above formula (I), S is the sulfonic acid group (SO$_2$OH) or its satisfied form, and n represents the average number of polymer repeat units in the polymer or copolymer. *Hackh's Chemical Dictionary*, Third Edition, edited by Julius Grant, published by The Blakiston Company, Inc., New York, in 1953, defines the term "salify" as "to form a salt." The term "satisfied form of the sulfonic acid group" as used herein means a form of the sulfonic acid group wherein the hydrogen atom of the hydroxyl group of the sulfonic acid group is replaced with a cation or cationic group. The salified form typically contains an ammonium group, an alkali metal atom, an alkaline earth metal atom, a transition metal atom, or an organic cation group. The polymer or copolymer has a molecular weight of generally above about 10,000 and preferably from about 25,000 to about 80,000. The polymer or copolymer has a degree of substitution (DS) of S groups of from about 0.2 to about 4. These sulfonated fluorinated polysulfone membranes are disclosed in U.S. Pat. No. 4,971,695 (Kawakami et al.), which teaches their use in separating gas mixtures such as air, as well as mixtures comprising hydrogen/nitrogen, hydrogen/methane, oxygen/nitrogen, ammonia/nitrogen, carbon dioxide/oxygen, carbon dioxide/methane, and hydrogen sulfide/methane. It is also known that these sulfonated fluorinated polysulfone membranes are used to separate gas mixtures of water/air and water/methane, with water permeating through the membrane.

Although sulfonated fluorinated polysulfone membranes have been used for separating streams, these membranes have not been used for separating and recovering hydrogen chloride from streams. Therefore, a method is sought that uses membranes for recovering and recycling hydrogen chloride from hydrocarbon-containing streams.

SUMMARY OF THE INVENTION

It has been discovered that sulfonated fluorinated polysulfone membranes have surprising and unexpected selectivity for separating compounds containing a halide, i.e., a Group 7A (IUPAC 17) element, such as hydrogen chloride, from streams that contain C$_1$–C$_7$ hydrocarbons. While it is already well known that sulfonated fluorinated polysulfone membranes are highly selective in permeating hydrogen from a mixture of hydrogen and methane, it has now been discovered that sulfonated fluorinated polysulfone membranes are nearly as selective in permeating hydrogen chloride from a mixture with methane as they are in permeating hydrogen from a mixture with methane. In addition, because the permeance of sulfonated fluorinated polysulfone membranes toward hydrocarbons decreases as the number of carbon atoms in the hydrocarbon increases, the sulfonated fluorinated polysulfone membranes are even more selective in permeating hydrogen chloride from a mixture with hydrocarbons that are heavier than methane. This invention takes advantage of these unexpected permeation characteristics of sulfonated fluorinated polysulfone membranes and, accordingly, in one of its embodiments comprises a process for separating hydrogen chloride from streams that contain C$_1$–C$_7$ hydrocarbons. The sulfonated fluorinated polysulfone membrane are polymers, including copolymers, having the polymer repeat unit of the previously mentioned formula (I).

The embodiment of this invention for separating hydrogen chloride from streams that contain C$_1$–C$_7$ hydrocarbons has wide applicability in the field of hydrocarbon processing for removing hydrogen chloride from light off gas or fuel gas streams in oil refineries. Such gas streams are generated in hydrocarbon conversion processes which use chloride-promoted catalysts. Particular examples of this embodiment comprise improved processes for the conversion of hydrocarbons using chloride-promoted catalysts in which hydrogen chloride is recovered from effluent streams and recycled to a catalytic hydrocarbon conversion zone by the use of sulfonated fluorinated polysulfone membranes. Specific hydrocarbon conversion processes to which this invention is applicable include processes for the isomerization, alkylation, reforming, and dehydrogenation of hydrocarbons. Compared to the prior art process of caustic scrubbing and adsorption for removing hydrogen chloride from such streams, this invention effectively eliminates or substantially decreases the significant costs of purchasing fresh caustic or fresh adsorbent and of disposing of spent caustic or spent adsorbent. This invention also dramatically reduces the make-up rate of chloride precursors, such as hydrogen chloride, carbon tetrachloride, and perchloroethylene to hydrocarbon conversion processes.

This invention is generally applicable to isomerization processes that use a performance enhancing material. Although this invention is useful in those isomerization processes which recycle hydrogen-rich gas from the reactor effluent separator to the reactor, this invention is particularly applicable to those isomerization processes which eliminate recycling from the reactor effluent separator to the reactor. Processes without such recycling use relatively low quantities hydrogen-rich gas on a once-through basis, as described in U.S. Pat. No. 4,929,794 (Schmidt et al.) and U.S. Pat. No. 5,026,950 (Schmidt et al.). The advantage of this invention, when used in the context of a once-through process, arises from the fact that hydrogen permeates readily through the sulfonated fluorinated polysulfone membrane, even more readily than hydrogen chloride. Thus, in the course of recovering hydrogen chloride from the stabilizer off gas stream of a once-through isomerization process, this invention also recovers and recycles nearly all of the hydrogen in the stabilizer off gas as well. Although the amount of hydrogen that is present in the stabilizer off gas of a once-through isomerization process is, of course, relatively small because these processes require comparatively little hydrogen-rich gas in any event, whatever hydrogen is recovered and recycled in the course of recovering and recycling hydrogen chloride further decreases the quantity of make-up hydrogen-rich gas that these once-through processes require.

This invention has other novel and particularly advantageous aspects in its application to hydrocarbon conversion processes. For each hydrocarbon conversion process to which this invention is applied, the benefits of this invention can be further enhanced by the use of a sweep stream, or purge, stream for the permeate side of the membrane. Although it is well known that the driving force for permeation of a component through a membrane can be increased by sweeping or purging the permeate side of the membrane with a gas containing a low mole fraction of that component, each particular hydrocarbon conversion process offers a wide range of streams for possible use as the sweep stream. In other words, many streams in a hydrocarbon conversion process meet the minimum criterion of a sweep stream, namely a low mole fraction of the permeating component. However, some streams are better than others for use as a sweep stream, and certain embodiments of this invention comprise a particularly advantageous choice of sweep stream. For example, in the case of an isomerization process, the most advantageous sweep stream is a portion of the stabilizer bottoms that has been vaporized, while in a motor fuel alkylation process, wherein an olefin such as propylene alkylates a paraffin such as isobutane in the presence of a stoichiometric excess of isobutane, the most advantageous sweep stream is a portion of the recycle isobutane that has been vaporized. These particular sweep streams are preferred because they maximize the driving force for permeation while minimizing the cost of utilities and without compromising in any way the benefits of this invention, namely retaining hydrogen chloride while minimizing hydrogen chloride contamination of gaseous products and effluent streams.

As has been suggested previously, it is believed that this invention has much wider applicability than the selective removal of merely hydrogen chloride or even of merely chloride-containing compounds. Because sulfonated fluorinated polysulfone membranes exhibit such high permeance for hydrogen chloride, it is believed that these membranes will likewise exhibit surprisingly high permeance for some other chlorine-containing hydrocarbons that have a non-zero resultant molecular moment. Thus, it is expected that sulfonated fluorinated polysulfone membranes can be used to separate a chlorine-containing hydrocarbon from a mixture of hydrocarbons having the same or more carbon atoms as the chlorine-containing hydrocarbon. Moreover, it is believed that this high permeance exhibited by sulfonated fluorinated polysulfone membranes for substituted hydrocarbons is not limited to chlorine-containing hydrocarbons. Accordingly, it is expected that sulfonated fluorinated polysulfone membranes can be used to separate a substituted hydrocarbon containing any Group 7A element, not only chlorine, from a mixture of hydrocarbons having the same or more carbon atoms as the substituted hydrocarbon. Thus, in its broadest scope, this invention comprises the use of sulfonated fluorinated polysulfone membranes to recover a permeable component containing a Group 7A element from a stream containing the permeable component and a $C_1$–$C_7$ hydrocarbon.

In a broad embodiment, this invention is a process for recovering a permeable component containing a Group 7A element from a feed stream containing the permeable component and a nonpermeable component. A feed stream, which comprises a permeable component containing a Group 7A element and a nonpermeable component, passes to a membrane separation zone. The membrane separation zone comprises a resin membrane comprising a polymer or copolymer containing the polymer repeat unit represented by the previously mentioned formula (I), wherein S is the sulfonic acid group or its salified form and wherein n represents the average number of polymer repeat units in the polymer or copolymer and wherein the polymer or copolymer has a molecular weight above about 10,000 and a degree of substitution of S groups of from about 0.2 to about 4. A permeate stream comprising the permeable component is withdrawn from the membrane separation zone.

In another embodiment, this invention is a process for the isomerization of a normal paraffin. Normal paraffins are introduced to an isomerization reaction zone, where normal paraffins are isomerized to branched paraffins having the same number of carbon atoms as the normal paraffins. The isomerization occurs in the presence of a chloride-containing catalyst. A reaction effluent stream is recovered from the isomerization reaction zone. The reaction effluent stream comprises branched paraffins, hydrocarbons having from 1 to 7 carbon atoms, and hydrogen chloride. At least a portion of the reaction effluent stream passes to a product separation zone, which operates at conditions to separate the entering paraffins. A recycle stream comprising hydrocarbons having from 1 to 7 carbon atoms and hydrogen chloride is withdrawn from the product separation zone. At least a portion of the recycle stream passes to a membrane separation zone comprising a resin membrane comprising a polymer or copolymer containing the polymer repeat unit represented by the previously mentioned formula (I). A permeate stream is withdrawn from the membrane separation zone. The permeate stream comprises hydrogen chloride. Branched paraffins are recovered from the process.

In another embodiment, this invention is a process for the alkylation of an alkylation substrate with an alkylating agent. An alkylating agent and an alkylation substrate pass to an alkylation reaction zone. In the alkylation reaction zone, the alkylating agent alkylates the alkylation substrate in the presence of a chloride-containing catalyst to form alkylate. A reaction effluent stream is recovered from the alkylation reaction zone. The reaction effluent stream comprises alkylate, hydrocarbons having from 1 to 7 carbon atoms, and hydrogen chloride. At least a portion of the reaction effluent stream passes to a product separation zone, which operates at conditions to separate the entering hydrocarbons. A recycle stream comprising hydrocarbons having from 1 to 7 carbon atoms and hydrogen chloride is withdrawn from the product separation zone. At least a portion of the recycle stream passes to a membrane separation zone comprising a resin membrane comprising a polymer or copolymer containing the polymer repeat unit represented by the previously mentioned formula (I). A permeate comprising hydrogen chloride is withdrawn from the membrane separation zone. Alkylate is recovered from the process.

INFORMATION DISCLOSURE

The isomerization of normal butane to isobutane is described in "UOP Butamer Process," Chapter 9.2, by Nelson A. Cusher, in the book entitled *Handbook of Petroleum Refining Processes,* Second Edition, edited by Robert A. Meyers, and published by McGraw-Hill in New York in 1997. The isomerizations of normal pentane to isopentane and of normal hexane to branched hexanes are described in "UOP Penex Process," Chapter 9.3, by Nelson A. Cusher in the Meyers book.

U.S. Pat. No. 4,929,794 (Schmidt et al.) and U.S. Pat. No. 5,026,950 (Schmidt et al.) describe isomerization processes that eliminate the recycling of a hydrogen-rich gas to the isomerization reactor.

U.S. Pat. No. 5,489,732 (Zhang et al.) discloses a fluidized solid bed motor fuel alkylation process that uses a halide. The teachings of U.S. Pat. No. 5,489,732 are incorporated herein by reference.

The use of nonporous, dense membranes in gas separation is described in the article entitled "Membrane Technology," written by Richard W. Baker, appearing at pp. 135–193 in Vol. 16 of the *Kirk-Othmer Encyclopedia of Chemical Technology,* 4$^{th}$ Edition, published by John Wiley, in New York, in 1995. This article teaches that the relative rate at which a component permeates through a nonporous, dense membrane depends on the diffusivity and solubility of the component in the membrane material.

It is well known that the driving force for the permeation of a component through a membrane can be increased by purging the low-pressure, or permeate, side of the membrane with a gas containing a low mole fraction of that component. See, for example, pages 1–13 in *Inorganic Membranes for Separation and Reaction,* by H. P. Hsieh, Membrane Science and Technology Series 3, Elsevier Science B. V., New York, 1996; and pages 308–326 in *Membrane Separation Processes,* ed. by P. Meares, Elsevier Scientific, New York, 1976. See also the following three articles by C. Y. Pan and H. W. Habgood: Ind. Eng. Chem., Fundamen., Vol. 13, No. 4, 1974, pp. 323–331; Can. J. Chem. Engg., Vol. 56, April 1978, pp. 197–209; and Can. J. Chem. Engg., Vol. 56, April 1978, pp. 210–217.

The article entitled "Pollution Control: Field Tests Show Membrane Processing Attractive," by T. E. Cooley and W. L. Dethloff, CEP, October, 1985, pp. 45–50, describes a normal butane isomerization process that passes a hydrogen-containing feed gas stream to an undisclosed membrane in order to recover hydrogen as permeate and recycle hydrogen to the process. The article teaches that when the feed gas stream to the membrane contained hydrogen chloride, two undesirable effects occurred: 65% of the hydrogen chloride permeated through the membrane, and high levels of hydrogen chloride impaired the membrane performance. To avoid these effects, this article teaches caustic washing of the feed gas stream to the membrane so that the feed gas stream is free of hydrogen chloride.

U.S. Pat. No. 4,971,695 (Kawakami et al.) discloses a sulfonated fluorinated polysulfone membranes and their use in separating gas streams. The teachings of U.S. Pat. No. 4,971,695 are incorporated herein by reference.

DETAILED DESCRIPTION OF THE INVENTION

Figure 1:
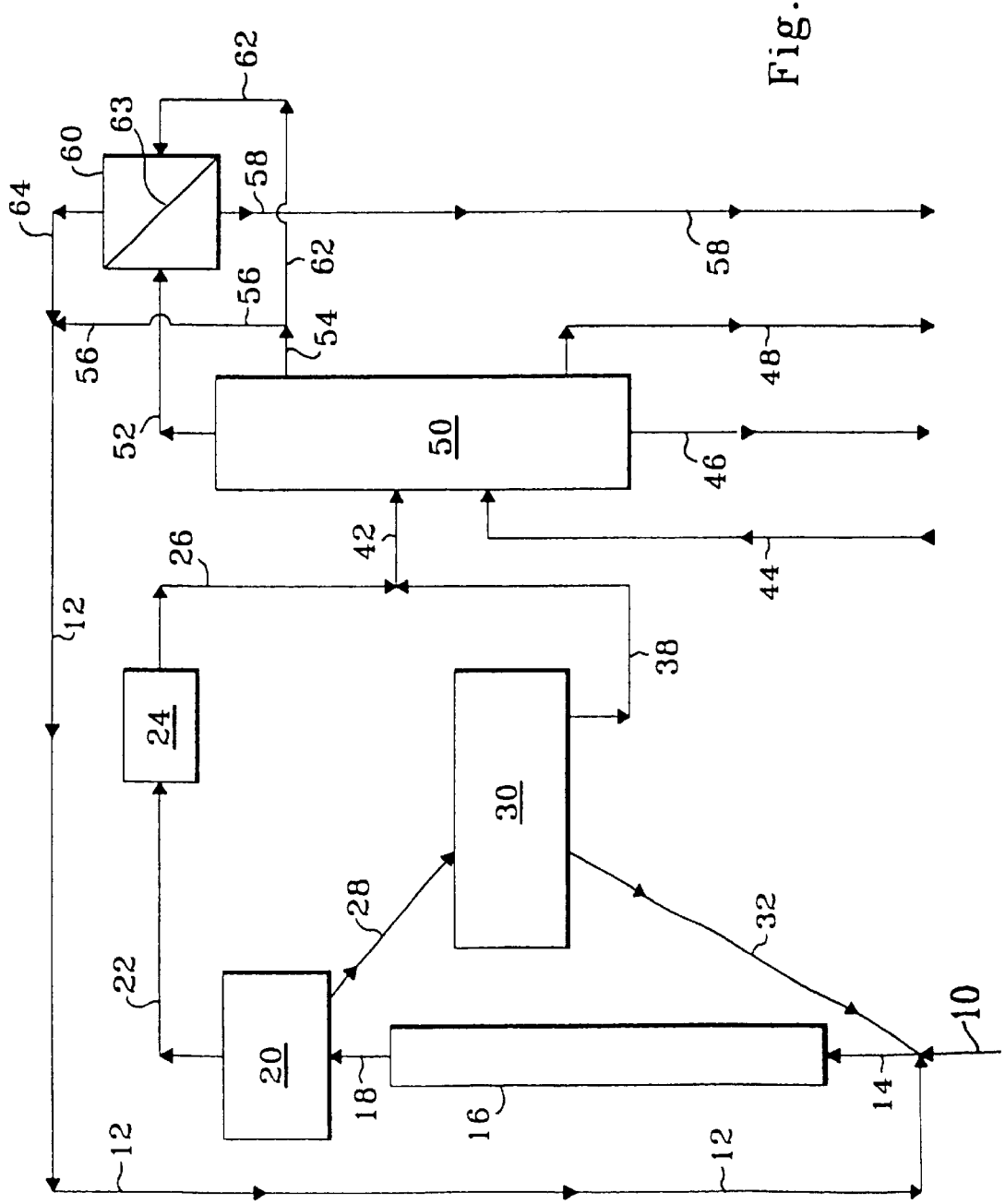
FIG. 1 is a process flow diagram of an alkylation process of this invention.

This invention recovers at least one permeable component from a stream that passes to a membrane separation zone and which is hereinafter referred to as the feed stream. In addition to the permeable component, the feed stream contains at least one nonpermeable component. The nonpermeable component is usually a light hydrocarbon, which means a hydrocarbon having between 1 and 7 carbon atoms and which is often referred to herein as a $C_1$–$C_7$ hydrocarbon. Although the hydrocarbon may be an aromatic or an olefin, the preferred hydrocarbon is a paraffin, which may be either normal or branched. The feed stream may be a mixture containing more than one light hydrocarbon. The total concentration of the light hydrocarbon(s) in the feed stream can generally be from 5 to 95 mol-% (0.05 to 0.95 mole fraction), and more typically from 60 to 90 mol-% (0.6 to 0.9 mole fraction).

The permeable component generally contains at least one atom of a Group 7A element, i.e., a halogen such as fluorine, chlorine, bromine, or iodine. Although the permeable component may contain any number of carbon atoms, the permeable component contains generally 7 or less carbon atoms, preferably 4 or less carbon atoms, and more preferably no carbon atoms. For permeable components having the same number of halogen atoms, the fewer the number of carbon atoms the greater is the permeance of the permeable component. Thus, it is expected that the permeance of chloromethane is greater than the permeance of chloroethane, which is in turn greater than the permeance of the chloropropanes. Although this invention is not limited by any particular theory, part of the explanation for this may be that the permeance depends on diffusivity, and the smaller the permeable component the greater is the diffusivity and hence the greater is the permeance. Another explanation for this may be that permeance depends on the resultant molecular moment of the permeable component, the polarity of certain bonds of the sulfonated fluorinated polysulfone membrane, and the tendency of a molecule having polar bonds to be more soluble and hence usually more permeable in a membrane having polar bonds. The benefit of the polar effect of the halogen atom(s) may decrease as the size of the permeable component increases.

For permeable components having the same number of carbon atoms, the greater the number of halogen atoms the greater is the permeance of the permeable component, provided that the steric orientation of the halogen atoms increases rather than decreases the dipole moment of the permeable component. Thus, it is expected that the permeance of 1,1-dichloroethane is greater than the permeance of chloroethane, because the presence of both chlorine atoms on the same carbon atoms is at least partially cumulative. In contrast, it is expected that the permeance of trans-1,2-dichloroethane is greater than that of cis-1,2-dichloroethane, because the steric orientation of the chlorine atoms decreases the dipole moment to nearly zero in the trans-isomer, but not in the cis-isomer.

For permeable components having the same number of carbon atoms and the same number of halogen atoms, it is expected that the greater the number of multiple bonds the greater is the permeance of the permeable component. Thus, a monoolefinic permeable component is expected to have a greater permeance than the corresponding saturated permeable component. Also for permeable components having the same number of carbon atoms and the same number of halogen atoms, it is expected that a noncyclic permeable component will have a greater permeance than a cyclic permeable component.

Preferably, the Group 7A element is chlorine. It is believed that preferred permeable components include those in which the position of the Group 7A element within the permeable component molecule results in a molecule having a non-zero molecular moment. Examples of such preferred permeable components containing a Group 7A element include hydrogen halides, such as hydrogen fluoride, hydrogen chloride, hydrogen bromide, and hydrogen iodide. Preferred permeable components include acyclic saturated halogen-substituted hydrocarbons having from 1 to 2 carbon atoms, including chloromethane (methyl chloride), dichloromethane (methylene chloride), trichloromethane (chloroform), chloroethane (ethyl chloride), and chloroethanes having from 1 to 5 chlorine atoms. Other permeable components include acyclic saturated halogen-substituted hydrocarbons having from 3 to 7 carbon atoms and one or more chlorine atoms, including chloropropanes, chlorobutanes, chloromethylpropanes, chloropentanes, chloromethylbutanes, chlorodimethylpropanes, and saturated hydrocarbons having 6 or 7 carbon atoms and substituted with one or more chlorine atoms (e.g., chlorohexanes and chloroheptanes).

Other suitable permeable components include cyclic saturated halogen-substituted hydrocarbons having from 1 to 7 carbon atoms and one or more chlorine atoms, such as chlorocylcopropanes, chlorocyclobutanes, chloromethylcyclopropanes, chlorocyclopentane, chlorodimethylcyclopropanes, chloromethylcyclobutanes, chloroethylcyclobutanes, chlorocyclohexanes and isomers thereof (e.g., chloromethylcyclopentanes, chlorodimethylcyclobutanes), and chlorocycloheptanes and isomers thereof (e.g., chlorodimethylcyclopentanes, chloromethylcyclohexanes).

Permeable components also include unsaturated analogs of the previously mentioned saturated halogen-substituted hydrocarbons which have from 1 to 7 carbon atoms and one or more chlorine atoms. These compounds may have one or more double bonds and one or more triple bonds. Acyclic compounds of this type include chloroethene, chloroethyne (chloroacetylene), 1,1-dichloroethene, cis-1,2-dichloroethene, and trichloroethene. Other acyclic compounds that have 3 to 7 carbon atoms and one or more chlorine atoms include chloropropenes, chloropropadienes, chloropropynes, chlorobutenes, chlorobutadienes, chlorobutynes, chlorobutadiynes, chloromethylpropenes, chloromethylpropynes, chloropentenes, chloropentynes, chloromethylbutenes, chloromethylbutynes, chlorodimethylpropenes, chlorodimethylpropynes, chlorohexenes, chlorohexynes, chlorohexadiynes, chloromethylpentenes, chloromethylpentynes, chlorodimethylbutenes, chlorodimethybutynes, chloroheptenes, chloroheptynes, chloromethylhexenes, chloromethylhexynes, chlorodimethylpentenes, chlorodimethylpentynes, chloroethylbutenes, and chloroethylbutynes.

Other chloride-containing compounds which have little or no resultant molecular moment on grounds of symmetry may also be present in the feed stream. These include molecular chlorine, tetrachloromethane (carbon tetrachloride); 1,2-dichloroethane (ethylene dichloride), trans-1,2-dichloroethene, tetrachloroethene (perchloroethylene), and hexachloroethane. It is expected that the permeance of compounds such as these will be greater than the permeance of the corresponding nonchloride-containing saturated hydrocarbons containing the same number of carbon atoms, due to the effect of the chloride atoms. However, it is also expected that the permeance of such components will be less than that of non-symmetrical chloride-containing permeable components that have the same number of carbon atoms and a larger resultant molecular moment but fewer chloride atoms.

For the permeable component, the resultant molecular moment is generally greater than zero, preferably greater than 0.5, and more preferably greater than 1.0. For the nonpermeable component, the resultant molecular moment is generally less than 0.75, preferably less than 0.35, and more preferably less than 0.1. Selected values of the resultant molecular moments in the gas phase for molecules containing a Group 7A (IUPAC 17) element are shown in Table 1A and of those for hydrocarbon molecules are shown in Table 1B. The values in Tables 1A and 1B are from the table starting on page E-63 in the *CRC Handbook of Chemistry and Physics*, 56$^{th}$ Edition, edited by Robert C. Weast, CRC Press, Cleveland, Ohio, 1975.

TABLE 1A

| Molecules Containing a Group 7A (IUPAC 17) Element | Selected Moment (Debyes) |
| --- | --- |
| Hydrogen fluoride | 1.82 |
| Hydrogen chloride | 1.08 |
| Hydrogen bromide | 0.82 |
| Hydrogen iodide | 0.44 |
| Chloromethane | 1.87 |
| Trichloromethane | 1.01 |
| Carbon tetrachloride | 0 |
| Chloroethane | 2.05 |
| 1,1,1-Trichloroethane | 1.78 |
| Chloroethene | 1.45 |
| cis-1,2-Dichloroethane | 1.90 |
| Chloroethyne | 0.44 |
| 2,2-Dichloropropane | 2.27 |
| 1,1-Dichlorocyclopropane | 1.58 |

TABLE 1B

| Hydrocarbon Molecules | Selected Moment (Debyes) |
| --- | --- |
| Methane | 0 |
| Ethane | 0 |
| Propane | 0.084 |
| n-Butane | ≦0.05 |

TABLE 1B-continued

| Hydrocarbon Molecules | Selected Moment (Debyes) |
|---|---|
| i-Butane (2-methylpropane) | 0.132 |
| 1-Butene | 0.34 |
| trans-2-Butene | 0 |
| 2-Methylpropane | 0.50 |

The feed stream may be a mixture containing more than one permeable component. The total concentration of the permeable component(s) in the feed stream can generally be from 0.1 mol-ppm to 70 mol-% ($10^{-7}$ to 0.7 mole fraction), but is more typically from 0.5 mol-ppm to 1 mol-% ($5 \times 10^{-7}$ to 0.01 mole fraction).

The feed stream may also, but need not, contain other additional components that permeate more readily or less readily than the permeable component. However, any other additional component should preferably not substantially interfere with the permeation of the permeable component or with the nonpermeation of the nonpermeable component. As used herein, a component substantially interferes with the permeation of the permeable component containing the Group 7A element when the presence of the component in the feed stream decreases the rate of permeation of the permeable component by more than 10% of the rate of permeation of the permeable component when the component is not present in the feed stream. Likewise, a component substantially interferes with the nonpermeation of the nonpermeable component when the presence of the component in the feed stream increases the rate of permeation of the light hydrocarbon by more than 10% of the rate of permeation of the nonpermeable component when the component is not present in the feed stream. In addition, any other component in the feed stream should preferably not have a deleterious effect on the physical or chemical properties of the membrane. Also, any other component in the feed stream should preferably not be a contaminant with respect to the process in which this invention is used, regardless whether the component exits the membrane separation zone in the permeate stream, the nonpermeate stream, and/or both streams.

Molecular hydrogen is a common example of an additional component which is often present in petroleum refinery streams that can be feed streams for this invention. The feed stream of this invention may contain generally from about 0 to about 99 mol-% hydrogen, and typically from about 75 to about 95 mol-% hydrogen. When hydrogen is present in the feed stream, hydrogen tends to permeate through the membrane employed in this invention, and thus most of the hydrogen in the feed stream exits the membrane separation zone in the permeate stream. Generally, this tendency of hydrogen to permeate with the permeable component containing the Group 7A element can be an advantage in many petroleum refinery processes. Isomerization, alkylation, reforming, and dehydrogenation processes are examples of refinery operations that emit some hydrogen in off gas streams that contain a compound with a Group 7A element. For such streams, it can be advantageous to recover and recycle not only the compound with the Group 7A element but also the hydrogen. Consequently, in embodiments of this invention that comprise these processes, the fact that the permeate stream contains both the permeable component as well as the hydrogen that enters with the feed stream makes the permeate stream even more useful and valuable than if it contained the permeable component alone.

The feed stream to the membrane separation zone preferably has a water concentration of less than 1 vol-ppm, and more preferably contains no water. Water can be removed from the feed stream by passing the feed stream through an adsorbent that selectively adsorbs water, such as 3A molecular sieve or silica gel. It is believed that water tends to increase the rate of corrosion in process equipment that is typically used in practicing this invention, such as vessels, piping, instrumentation, and membrane housings or modules. It is believed that water, in combination with components that contain a Group 7A element, especially molecular halogens (e.g., molecular fluorine, chlorine, bromine, and iodine) or hydrogen halides (e.g., hydrogen fluoride, hydrogen chloride, hydrogen bromide, and hydrogen iodide), tends to rapidly corrode iron-containing and other metal-containing equipment, and that the corrosion products can have a deleterious effect on the membrane. Although corrosion-resistant alloys could be used to decrease the rate of corrosion, generally such alloys are expensive and therefore it is more economical to invest in feed stream drying equipment than in expensive corrosion-resistant equipment.

The feed stream also preferably contains no inorganic iron-containing species because it is believed such species may tend to react with a Group 7A (such as chloride) and have a serious deleterious effect on the selectivity of the membrane. It is believed that other species in the feed stream, comprising other Group VIII (IUPAC 8–10) elements or Group I B through VIII B (IUPAC 3 through 7, 11, and 12) elements may also have a detrimental effect on the membrane and, therefore, should also preferably not be present in the feed stream. Methods to remove these species from the feed stream are well known and include filtration.

The feed stream may be obtained from at least a portion of the effluent of a reactor in a reaction zone of a hydrocarbon conversion process, such as a process for isomerization, alkylation, reforming, or dehydrogenation of hydrocarbons. As used herein in the context of a stream and unless indicated otherwise, the term "portion" means an aliquot portion of the stream having the same composition as the stream or a portion of the stream having a different composition as the stream. Depending on the particular hydrocarbon conversion process, the feed stream may be an aliquot portion of the reactor effluent, or the feed stream may be a stream which is recovered from a separation zone which separates the reactor effluent and which has a different composition from the reactor effluent. For example, the feed stream may be obtained from the effluent of an isomerization reactor for isomerizing a normal paraffin to a branched paraffin, in which case the isomerization reactor effluent and/or the feed stream may contain hydrogen chloride and, in addition to the desired branched paraffin product, other $C_1$ to $C_7$ hydrocarbons, depending on the composition of the charge stock to and also on the operating conditions of the isomerization reaction zone. The feed stream may also be obtained from the effluent of an alkylation reactor in an alkylation reaction zone for alkylating an alkylation substrate with an alkylating agent. In this case, the reactor effluent and/or the feed stream may contain the desired alkylate product, other $C_1$ to $C_7$ hydrocarbons, and hydrogen chloride.

The feed stream passes to a membrane separation zone comprising a resin membrane comprising a polymer or copolymer containing the polymer repeat unit of the previously mentioned formula (I). Sulfonated polysulfone polymers can be prepared by sulfonation methods known in the art; see, for example, U.S. Pat. No. 3,709,842, wherein Quentin describes a preparation of polymers in which part of the aromatic rings are substituted with hydroxysulfonyl radicals (—$SO_3H$, also called sulfonic groups). Additional methods can be found in E. E. Gilbert, *Sulfonation and Related Reactions,* R. E. Krieger Publishing Co., New York (1977) and A. Noshay and L. M. Robeson, J. of Applied Polymer Science, V20, p. 1885 (1976). In general, the sulfonation may be carried out by simple admixture of a solution or suspension of the polysulfone with a sulfonation agent in an inert solvent system. Sulfur trioxide, chlorosulfonic acid, and oleum are representative sulfonation agents. The temperature at which sulfonation takes place is less critical for polysulfone polymers of this invention due to good chemical resistance towards degradation. An advantageous temperature is within the range of from −13 to 176° F. (−25 to 80° C.), preferably from 32 to 122° F. (0 to 50° C.). The sulfonated product polymer is usually separated from the reaction mixture by conventional techniques such as filtration, washing, and drying.

The sulfonated polysulfone containing the polymer repeat unit of the previously mentioned formula (I) is shown to have sulfonate groups on the phenyl moiety distal to the sulfone linking group. Although substitution at these locations theoretically occurs first, the sulfonate groups may substitute at other positions and in other phenyl moieties of the polymer during sulfonation. The degree of substitution DS of the sulfonated hexafluoro polymers containing the polymer repeat unit of the previously mentioned formula (I) is a measure of the average number of polymer repeat units present in the polymer composition that have been sulfonated. Typically the degree of substitution is on average from about 0.2 to about 4, preferably from about 0.5 to about 2. Thus, if on average half of the polymer repeat units of the previously mentioned formula (I) are sulfonated, the degree of substitution is 0.5.

The fluid separation membranes used in the processes of this invention can be of dense film or of any form known to those skilled in the art. Further, it can be a composite membrane, an asymmetric membrane, or a homogeneous or isotropic membrane. The membranes may be in spiral form, flat sheet, or other configurations, as well as in hollow fiber or tubular form. Those skilled in the art are aware of the many methods available for their production and know how to prepare the membranes in any of these forms.

The isotropic and asymmetric type membranes used in the process of this invention are generally comprised essentially of a single permeable membrane material, the sulfonated hexafluoro bis-A polysulfone polymer containing the polymer repeat unit of the previously mentioned formula (I), which is capable of selectively separating at least one component from a fluid mixture containing said at least one component in admixture with other components. Asymmetric membranes used in the process of this invention are distinguished by the existence of two or more morphological regions within the membrane structure; one such region comprising a thin relatively dense semipermeable skin capable of selectively permeating at least one component from a fluid mixture containing said at least one component in admixture with other components, and the other region comprising a less dense, porous, essentially nonselective support region that serves to preclude the collapse of the thin skin region of the membrane during use. Composite membranes generally comprise a thin layer or coating of a suitable semipermeable membrane material, the sulfonated hexafluoro bis-A polysulfone polymer containing the polymer repeat unit of the previously mentioned formula (I), superimposed on a porous substrate.

The sulfonated fluorinated polysulfones containing the polymer repeat unit of the previously mentioned formula (I) can be used as a pure membrane forming material, an admixture of several sulfonated polysulfones, or in a mixture with other organic or inorganic materials. The sulfonated fluorinated polysulfones will typically represent more than 50 percent by weight of the composition of the membrane material and preferably more than 70 percent by weight of the composition of the membrane material. Some typical examples of inorganic materials that can be used in a mixture with sulfonated fluorinated polysulfones are inorganic acids, such as sulfuric or phosphoric acid. Organic materials useful as admixtures with the sulfonated fluorinated polysulfones can be high molecular weight polymers that can be neutral or can contain ionic groups, e.g., polyvinyl pyridine, polyethylene imine, polyethylene glycol, polypropylene glycol, etc., or low molecular weight materials and plasticizers, for example, organic salts, polyhydric alcohols such as glycerine, low molecular weight amines such as ethylenediamine, diethylene triamine, acridine, piperazine, pyridine, etc.

Flat sheet membranes are readily prepared from solutions of the sulfonated hexafluoro bis-A polysulfone polymer containing the polymer repeat unit of structure(I) in a suitable solvent, e.g., methoxyethanol, dimethylformamide, and the like, by casting the solution and evaporating the solvent, and thereafter drying and curing the case film, either under vacuum, at elevated temperature, or a combination of both. Such thin film membranes can vary in thickness from about 0.5 mil to about 10 mils or more, preferably from about 1 mil to about 3 mils. As used herein, the term "mil" means $\frac{1}{1000}^{th}$ inch.

Flat sheet membranes are not, however, the preferred form for use in commercial applications of this invention. In large scale commercial applications, hollow fiber permeable membranes are generally more desirable because they provide a significantly larger surface area per volume unit when fabricated as modules. The composite hollow fiber membranes that comprise a porous hollow fiber support having a permeable membrane layer on the surface thereof are advantageously used for fluid separations. The methods for their production are well known (See for example, *Hollow Fibers Manufacture and Applications,* ed. J. Scott, Noyes Data Corporation, New Jersey, 1981, p. 264 et seg.). Porous hollow fiber polysulfone substrates are particularly useful in the preparation of composite membranes. Porous polysulfone hollow fibers can be produced from solutions of the polysulfone in a solvent/nonsolvent mixture, as is known in the art, using the procedure described by I. Cabasso et al. in "Composite Hollow Fiber Membranes", Journal of Applied Polymer Science, 23, 1509–1523 and in "Research and Development of NS-1 and Related Polysulfone Hollow Fibers For Reverse Osmosis Desalination of Seawater" PB 248,666, prepared for the Office of Water Research and Technology, Contract No. 14303165, U.S. Department of the Interior, July 1975. The well known tube-in-tube jet technique can be used for the spinning procedure, with water at about room temperature being the outside quench medium for the fibers. The quench medium in the center bore of the fiber can be air. Quenching can be followed by extensive washing to remove pore forming material. Following the wash, the hollow fibers can be dried at elevated temperature by passage through a hot air drying oven.

A suitable membrane material for use in this invention is called 6F-SPS (6-fluoro sulfonate polysulfone) membrane material, which is manufactured to custom order by Innovative Membrane Systems Inc., of Norwood, Mass. USA, and is available for use in practicing this invention from UOP LLC, of Des Plaines, Ill., USA.

The operating conditions for the membrane separation zone include at least a partial gas phase operation both on the nonpermeate side and on the permeate side of the membrane. Preferably, all streams on both sides of the membrane are gas phase. The temperature of the membrane separation zone is generally from 50 to 250° F. (10 to 121° C.), and preferably from 100 to 180° F. (38 to 82° C.). The pressure on the nonpermeate side, which is generally the higher pressure side, of the membrane separation zone is generally from 50 to 1000 psi(g) (345 to 6895 kPa(g)) and typically from 250 to 450 psi(g) (1724 to 3103 kPa(g)). On the permeate side, which is generally the lower pressure side, of the membrane separation zone, the pressure is generally from 0 to 500 psi(g) (0 to 3448 kPa(g)) and typically from 5 to 50 psi(g) (34.5 to 345 kPa(g)).

The permeate stream contains the permeable component, which as previously mentioned, comprises at least one atom of a Group 7A element. The mole fraction of the permeable component in the permeate stream is generally greater than the mole fraction of the permeable component in the feed stream. However, depending on the flow rate of a sweep stream, if any, the mole fraction of the permeable component in the permeate stream may be less than that in the permeate stream because a sweep stream can dilute the permeate stream.

In order to increase the driving force for permeation through the membrane of the permeable component, a sweep, or purge, stream is preferably introduced to the membrane separation zone on the permeate side of the membrane. The sweep stream increases the driving force for permeation by decreasing the partial pressure of the permeable component containing the Group 7A element on the permeate side of the membrane. The ideal flow rate of the sweep stream depends on a number of factors, including the nonpermeate pressure, the permeate pressure, the selectivity of the membrane, and the nonpermeate stream flow rate. The ratio of the volumetric flow rate of the sweep stream to the volumetric flow rate of the feed stream is generally from about 0.001 to about 1000. All other factors being the same, as this volumetric ratio increases the concentration of the permeable component in the permeate stream decreases, because of the dilution effect of the sweep stream in the permeate stream.

As mentioned previously, this invention is applicable to a number of hydrocarbon conversion processes, and the choice of the preferred or optimum sweep stream depends on the particular hydrocarbon conversion process. For a hydrocarbon conversion process that uses this invention to recover and recycle a permeable component, preferably the product of the mole fraction of the permeable component in the sweep stream and the pressure at the permeate side of the membrane is not greater than the product of the mole fraction of the permeable component in the nonpermeate stream and the pressure at the nonpermeate side of the membrane.

It is believed that for most processes that are expected to use this invention in order to recover and recycle hydrogen chloride, the charge stock to the process meets the minimum requirement for a sweep stream. The term "charge stock" as used herein refers to a stream containing reactants that is charged to the reaction zone of a hydrocarbon conversion process. For example, in an alkylation process charge stocks include the stream containing the alkylation substrate and the stream containing the alkylating agent, each of which is charged to the reaction zone. In an isomerization process, the charge stocks include the stream containing the straight chain paraffinic hydrocarbon, as well as any streams containing makeup hydrogen that are charged to the reaction zone. This invention is applicable to those and other processes that require a minimum level of chloride in the environment of the reaction zone and in which in the absence of this invention the inflow of chloride to the reaction zone is less than the outflow of chloride from the reaction zone. In these processes, the fact that the inflow of chloride is relatively low is generally indicative of the fact that the charge stock either contains no chloride or has a relatively low mole fraction of chloride. Little or no chloride in the charge stock, in turn, tends to make the charge stock more suitable for use as a sweep stream.

This generalization about the suitability of the charge stock for use as the sweep stream applies not only to the charge stock but to other streams that are inputted into the process as well. Other input streams to the process, such as a hydrogen or nitrogen purge stream, would likewise generally have a relatively low mole fraction of hydrogen chloride and would usually be suitable for use as a sweep stream also. However, the charge stock generally has the largest flow rate of the input streams that could be possibly used as the sweep stream. The relatively large flow rate of the charge stock makes the charge stock one of the better possible sweep streams from the viewpoint of process control, because the required flow rate of the sweep stream is generally such a small fraction of the total flow rate of the charge stock that a slip stream of the charge stock is sufficient to satisfy the sweep flow requirements. Thus, if a slip stream of the charge stock passes to the membrane separation zone as the sweep stream and if the effluent of the permeate side of the membrane separation zone combines with the remainder of the charge stock and passes to the reaction zone, then the flow rate of the slip stream can be adjusted as needed for sweeping without changing the total flow rate of charge stock to the process.

As a practical matter, however, the charge stock may not be the most desirable stream of the process for use, in whole or in part, as the sweep stream to the membrane separation zone. The charge stock may be not be the preferred stream because it contains contaminants or foulants that would interfere with the performance of the membrane. Also, the charge stock may be undesirable because it is at a different temperature, pressure, or phase than that which exists on the permeate side of the membrane separation zone. Thus, it may be especially advantageous to choose some other particular stream of the process for use as the sweep stream. Of course, any other stream that is a candidate for the sweep stream must already meet the previously described minimum requirement for the sweep stream—namely that of providing a relatively low partial pressure of hydrogen chloride on the permeate side of the membrane separation zone. One or more other streams in the process, such as the overhead or bottoms stream of a distillation column in the product separation zone, may contain fewer contaminants or foulants than the charge stock and may already be at the desired operating temperature, pressure, and phase as the permeate side of the membrane separation zone. Thus, the sweep stream may comprise hydrogen or hydrocarbons having from 1 to 7 carbon atoms, may be formed from at least a portion of the nonpermeate stream, or may in an isomerization process comprise the branched paraffin. Accordingly, in several of its embodiments, this invention is a process for converting hydrocarbons by isomerization or by alkylation, in which hydrogen chloride is recovered and recycled to the isomerization or alkylation zone, respectively, and in which the process is especially benefited by a particularly advantageous selection of the sweep stream from any of a number of other streams in the process.

In a hollow fiber permeable membrane configuration, the arrangement of the point of introduction of the feed stream and the point of withdrawal of the permeate stream relative to the membrane can result in cocurrent flow or cross flow of the feed stream and the permeate stream, but preferably the arrangement results in countercurrent flow of the feed stream and the permeate stream. In addition, while some back-mixing can occur on both the nonpermeable and permeate sides of the membrane, preferably the feed stream flows in a plug flow manner with little or no back-mixing on the nonpermeate side of the membrane, and likewise the permeate stream flows in a plug flow manner with little or no back-mixing on the permeate side of the membrane. The nonpermeate side of a hollow fiber permeable membrane may be either the inside or the outside of the hollow fiber, but preferably the nonpermeate side is the outside of the hollow fiber and thus the permeate side is the inside of the hollow fiber. Preferably, differences in pressure between locations along the length of the nonpermeate side of the membrane, or between locations along the length of the permeate side of the membrane, are relatively small in comparison to (i.e., less than 5% of) the difference at any location along the membrane between the pressure on the nonpermeate (high-pressure) side of the membrane and the pressure on the permeate (low pressure) side of the membrane. Accordingly, in a preferred arrangement of a hollow fiber permeable membrane, the feed stream is introduced at one end of the hollow fiber and flows in a plug-flow manner along the length of and on the outside of the hollow fiber, while the permeable component is collected along the length of the inside of the hollow fiber and the permeate stream flows in a plug flow manner along the length of the inside of the hollow fiber and is withdrawn from the same end of the hollow fiber at which the feed stream is introduced. When a sweep stream is used in the preferred arrangement, the sweep steam is introduced into the inside of the hollow fiber at the end of the hollow fiber that is opposite from the end at which the feed steam is introduced and the permeate steam is withdrawn. The sweep stream then flows inside and along the length of the hollow fiber in a plug flow manner and is withdrawn with the permeate stream.

Figure 2:
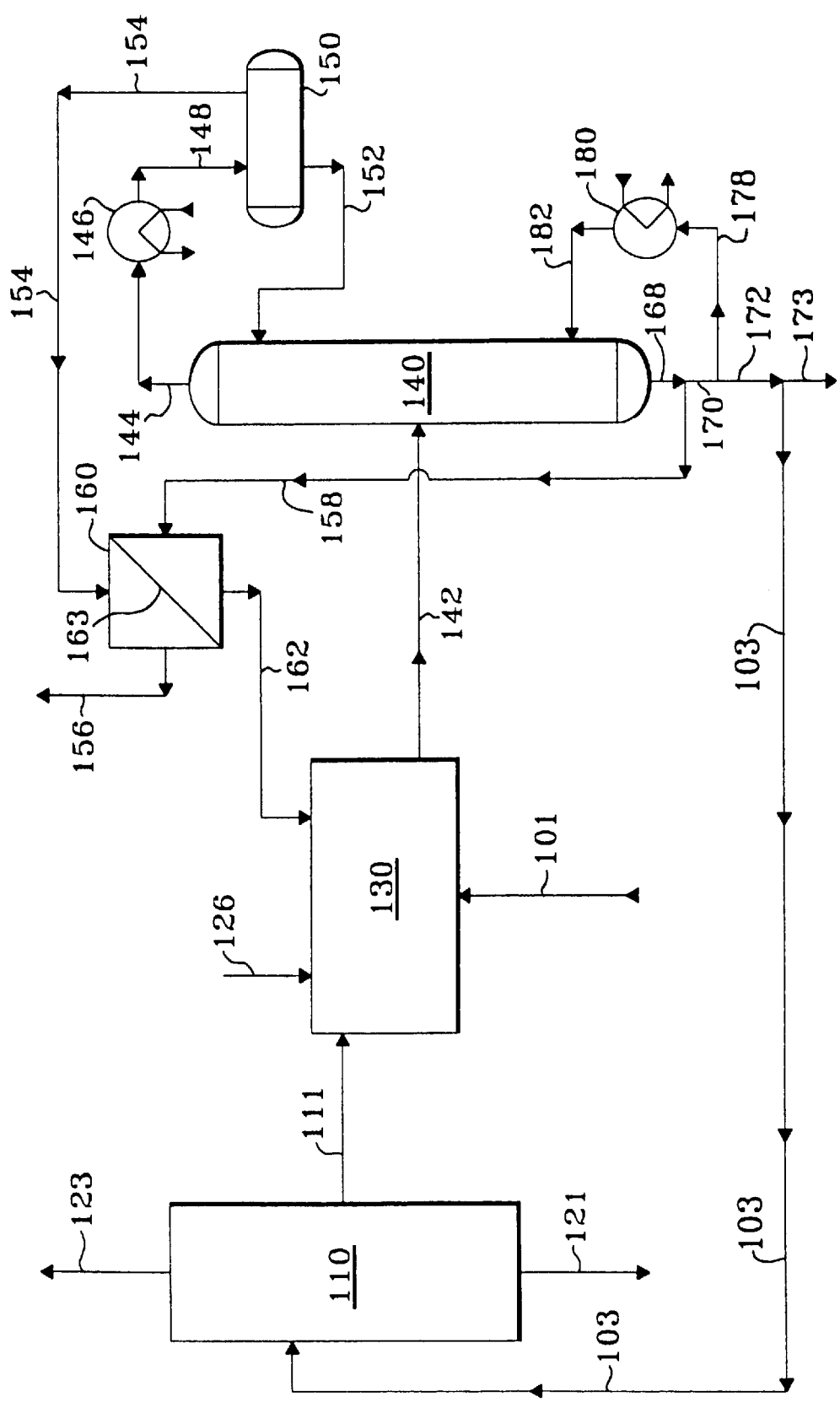
FIG. 2 is a process flow diagram of a butane isomerization process of this invention.
Figure 3:
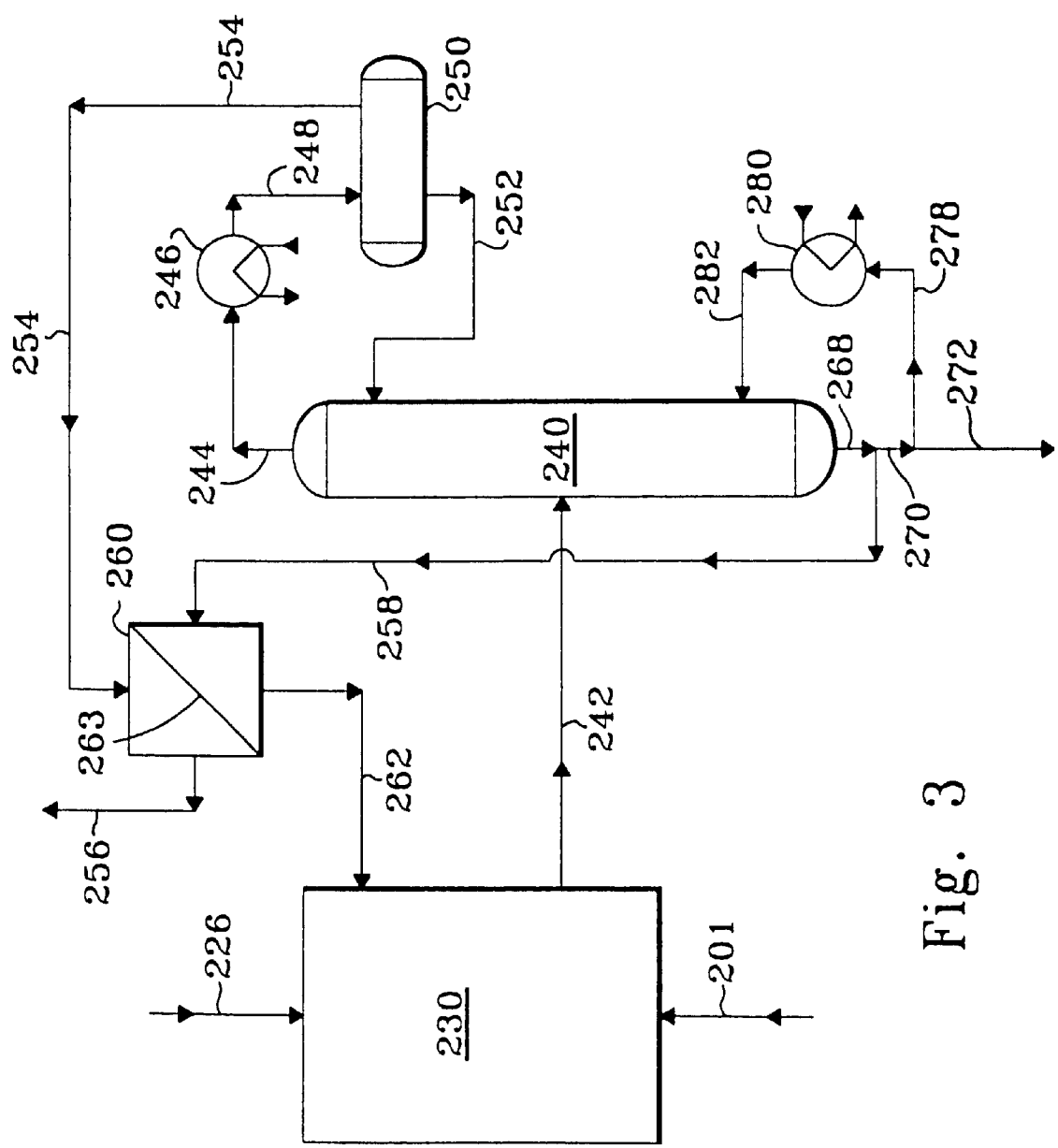
FIG. 3 is a process flow diagram of a pentane and hexane isomerization process of this invention.

FIGS. 1, 2, and 3 illustrate, respectively, preferred embodiments of this invention for use in the alkylation of isoparaffins with olefins, in butane isomerization, and in pentane and hexane isomerization. For clarity and simplicity, some items associated with the operation of the embodiments have not been shown. These items include flow and pressure control valves, pumps, heat exchangers, temperature and pressure monitoring systems, vessel internals, etc., which may be of customary design. FIGS. 1, 2, and 3 are not intended to limit the scope of the present invention as set forth in the claims.

Referring now to FIG. 1, an olefinic charge stock comprising an alkylating agent ($C_3$–$C_5$ olefin) enters the process through a line 10. The olefinic charge stock combines with a recycle stream comprising an alkylation substrate ($C_4$–$C_5$ branched paraffin) and hydrogen chloride flowing through a line 12 and a regenerated catalyst stream comprising at least partially regenerated catalyst particles that flows through a line 32. The catalyst particles contain chloride. The flow rate of catalyst particles through the line 32 is controlled by one or more fluid-controlled valves (not shown), which are also called nonmechanical valves. Nonmechanical valves, which include L valves, J valves, or K valves, are described in an article entitled "L Valves Characterized for Solid Flow," beginning at page 149 in the March, 1978 issue of *Hydrocarbon Processing*, in the text entitled Gas Fluidization Technology, edited by D. Geldart and published by John Wiley and Sons in 1986, and in U.S. Pat. No. 4,202,673. A slip stream (also not shown) of the recycle stream can be used as the control fluid for each nonmechanical valve.

The combined mixture of $C_4$–$C_5$ branched paraffins, $C_3$–$C_5$ olefins, and catalyst particles flows through a line 14 and enters a transport reactor 16, where $C_3$–$C_5$ olefins alkylate $C_4$–$C_5$ branched paraffins in at least a partial liquid phase to produce an alkylate comprising at least some $C_7^+$ hydrocarbons. Transport reactors are well known in continuous catalytic hydrocarbon conversion processes. In a transport reactor, the catalyst bed as a whole moves and is transported with a fluid phase. Thus, a transport reactor can be contrasted with a fixed bed catalytic reactor and with an ebulated bed catalytic reactor. In a fixed bed reactor the catalyst particles do not move, and in an ebulated bed reactor the catalyst particles are suspended in a fluid but the settling velocity of the catalyst particles balances the fluid upflow velocity so that the catalyst bed as a whole is not transported with the fluid phase. Although it is generally the case that the direction of catalyst flow through a transport reactor is upward, the direction may also be downward, horizontal, a direction that is intermediate between vertical and horizontal, or a combination of these directions.

Transport reactor 16 is preferably a riser-reactor, and is referred to hereinafter as riser-reactor 16. A riser-reactor is a transport reactor in which the direction of catalyst flow is upward. Riser-reactors are commonly used in hydrocarbon processing, such as fluidized catalytic cracking and more recently in motor fuel alkylation. In a common arrangement, a fluid hydrocarbon reactant engages a solid hydrocarbon conversion catalyst at the bottom of the riser-reactor and transports the catalyst in a fluidized state up the riser-reactor. During the ascent through the riser-reactor, the catalyst promotes certain desired conversion reactions among the reactants in order to produce desired products and, in addition, heavy hydrocarbons tend to deposit on the catalyst, at least partially deactivating the catalyst. A stream of catalyst containing heavy hydrocarbon deposits, alkylate, $C_4$–$C_5$ branched paraffins, $C_1$–$C_3$ hydrocarbons, organic chloride-containing compounds, and hydrogen chloride discharges from the top of the riser-reactor 16.

The effluent of riser-reactor 16 flows through a line 18 and enters a reactor effluent separation zone 20, which separates the riser-reactor effluent into a hydrocarbon-containing stream that flows through a line 22 and a spent catalyst stream containing catalyst having heavy hydrocarbon deposits that flows through a line 28. The stream in the line 22 contains alkylate, $C_4$–$C_5$ branched paraffins, $C_1$–$C_3$ hydrocarbons, hydrogen chloride, organic chloride-containing compounds, such as butyl chlorides, pentyl chlorides, and chloride-containing compounds having up to about 12 or more carbon atoms. In order to decompose these organic chlorides, some or all of the stream in the line 22 flows to a catalytic dechlorination zone 24, where at least a portion of the organic chloride-containing compounds are decomposed into hydrogen chloride and one or more hydrocarbons. Any suitable catalytic dechlorination zone and dechlorination catalyst known to a person of ordinary skill in the art may be used, and the choice of a particular dechlorination zone or catalyst is not critical to the success of this invention. Some or all of the dechlorination zone effluent passes through a line 26, combines with a hereinafter-described regeneration effluent stream that flows through a line 38, and the combined stream flows through a line 42 to a product separation zone 50.

The spent catalyst stream that flows through the line 28 enters a regeneration zone 30 for the purpose of restoring the activity or selectivity of the catalyst particles. The catalyst particles in the spent catalyst stream are usually at least partially deactivated by the deposition of heavy hydrocarbons on the catalytically active sites of the catalyst. Heavy hydrocarbons are hydrocarbons having a carbon number greater than that of the desired alkylate product. In order to remove alkylate and heavy hydrocarbons from the catalyst particles, the regeneration zone 30 may comprise one or more subzones, which are not shown in FIG. 1. For example, the regeneration zone may be subdivided into three subzones: an upper subzone zone, a middle subzone, and a lower subzone. The upper subzone may be a liquid-phase, or mild, regeneration zone, where the catalyst particles are contacted with hot, hydrogen-saturated isobutane liquid in order to remove alkylate and at least a portion of the heavy hydrocarbons from the catalyst particles. The middle zone may be a flushing zone, where the catalyst particles are contacted with isobutane in order to remove residual hydrogen from the void volume and the pore volume of the catalyst. The lower zone may be a catalyst withdrawal zone, from which catalyst particles are withdrawn and recirculated to the riser-reactor 16. Where the regeneration zone 30 is subdivided into two or more zones, conventional fluid and particle flow distributors may be used to divide or separate the zones from each other. Such conventional distributors include pipe distributors, conical baffles, and annular baffles. Annular baffles are disclosed in U.S. Pat. No. 4,662,081 (Greenwood), U.S. Pat. No. 4,665,632 (Greenwood), and U.S. Pat. No. 5,397,458 (Micklich et al.). The at least partially regenerated catalyst that is withdrawn from the regeneration zone 30 forms the previously mentioned regenerated catalyst stream which flows through the line 32.

The regeneration of the catalyst particles in regeneration zone 30 produces a regeneration effluent stream that leaves the regeneration zone 30 in a line 38. The composition of the regeneration effluent stream will depend on the particular regeneration steps, conditions, and streams that are employed to regenerate the catalyst particles. Typically, the regeneration effluent stream comprises branched $C_4$–$C_5$ paraffins, a small quantity of the heavy hydrocarbons that were removed from the catalyst, hydrogen, and hydrogen chloride. The regeneration effluent stream passes to the product separation zone 50 through the lines 38 and 42, as described previously.

The product separation zone 50 is fed by two streams, namely the stream flowing through the line 42 and a paraffinic charge stock comprising a mixture of normal and branched $C_4$–$C_5$ paraffins that enters through a line 44. The product separation zone 50, in turn, produces four outlet streams: a bottom stream, a heavy sidecut stream, a light sidecut stream, and an overhead stream. The bottom stream contains alkylate and a small amount of heavy hydrocarbons and exits the product separation zone 50 through a line 46. The heavy sidecut stream contains normal $C_4$–$C_5$ paraffins and possibly $C_3$ hydrocarbons, exits the product separation zone 50 through a line 48, and is rejected from the process. The light sidecut stream contains branched $C_4$–$C_5$ paraffins and possibly hydrogen chloride, and exits the product separation zone 50 through a line 54. Most of the light sidecut stream passes through a line 56, combines with a hereinafter-described permeate stream in a line 64, and is recycled to the inlet of the riser-reactor 16 through the lines 12 and 14, as described previously. Alternatively, the streams in lines 56 and 64 may be routed separately rather than in combination to the riser-reactor 16. The remainder of the light sidecut stream passes through a line 62 and serves as the sweep stream to the membrane separation zone 60, which is described hereinafter. The overhead stream of the product separation zone 50 is gaseous and contains hydrogen, hydrogen chloride, $C_1$–$C_3$ hydrocarbons, and possibly branched $C_4$–$C_5$ paraffins. The overhead stream generally contains a higher concentration of hydrogen chloride than the light sidecut stream. The overhead stream exits through a line 52 and is the inlet stream to the membrane separation zone 60.

In practice, the product separation zone 50 typically comprises two fractionation columns: an isostripper and a depropanizer. In a process with such a two-column zone, the stream in the line 42 and the paraffinic charge stock in the line 44 pass to the isostripper. The isostripper produces a bottom stream comprising alkylate and a small amount of heavy hydrocarbons, a heavier-boiling sidecut stream comprising normal $C_4$–$C_5$ paraffins, a lighter-boiling sidecut stream comprising branched $C_4$–$C_5$ paraffins, and an overhead stream comprising hydrogen chloride, hydrogen, and $C_1$–$C_3$ hydrocarbons. The bottom stream and the heavier-boiling sidecut stream are recovered from the process. The lighter-boiling sidecut stream is recycled to the inlet of the riser-reactor 16, and the isostripper overhead stream passes to the depropanizer. The depropanizer separates the overhead stream from the isostripper into a gaseous depropanizer overhead stream having the composition of the stream in the line 52 in FIG. 1, which is the inlet stream to the membrane separation zone 60. The depropanizer also produces a bottom stream comprising isobutane that is recycled to the inlet of the riser-reactor 16. In addition, the depropanizer produces a sidecut stream comprising isobutane vapor, which functions as the sweep stream in the line 62 in FIG. 1 for the membrane separation zone 60.

The function of the membrane separation zone 60 is to selectively separate the hydrogen and hydrogen chloride from the light hydrocarbons in the inlet stream flowing in the line 52. The membrane separation zone 60 contains a membrane 63 that comprises a resin membrane comprising a polymer or copolymer containing the polymer repeat unit of the previously mentioned formula (I). Light hydrocarbons such as $C_1$–$C_3$ hydrocarbons in the inlet stream in the line 52 do not selectively pass through the membrane 63 and are withdrawn in a nonpermeate stream in a line 58. These light hydrocarbons may be used as fuel, either directly or after scrubbing with caustic to remove trace amounts of hydrogen chloride. Most of the hydrogen chloride that is present in the inlet stream in the line 52 selectively passes through the membrane 63 and is recovered in the permeate stream, which exits the membrane separation zone 60 in a line 64. Hydrogen that is present in the inlet stream in the line 52 also tends to selectively pass through the membrane 63 and is also recovered in the permeate stream. In order to improve the driving force for the selective passage of hydrogen chloride through the membrane, the previously mentioned sweep stream passes through the line 62 to the permeate side of the membrane 63. The sweep stream is preferably a vapor, such as gaseous $C_4$–$C_5$ branched paraffins, and thus if the light sidecut stream in the line 54 is liquid phase, then means (not shown in FIG. 1) may be provided to vaporize the stream in the line 62. Because the sweep stream has a low mole fraction of hydrogen chloride, the sweep stream tends to dilute the partial pressure of hydrogen chloride on the permeate side of the membrane 63, thereby enhancing the passage of hydrogen chloride through the membrane 63. The use of a sweep stream comprising $C_4$–$C_5$ branched paraffins results in the permeate stream in line 64 also containing branched $C_4$–$C_5$ branched paraffins.

FIG. 2, as previously mentioned, is a preferred embodiment of this invention for use in butane isomerization.

Referring now to FIG. 2, a recycle stream comprising normal butanes and isobutane flows through a line 103 from the bottom of a stabilizer column 140, as described hereinafter, and enters a deisobutanizer zone 110. A normal butane stream is withdrawn from the deisobutanizer zone 110 and passes to an isomerization reaction zone 130 via a line 111. In addition to the normal butane stream in the line 111, the deisobutanizer zone 110 also produces an isobutane stream comprising isobutane that is recovered from the process via a line 123 and a heavier stream comprising higher-boiling $C_4+$ hydrocarbons that is recovered from the process via a line 121. A dried butane charge stock enters the process through a line 101, and is charged to the isomerization reaction zone 130. In addition, makeup hydrogen, also dried, enters the isomerization reaction zone 130 via a line 126, and a hereinafter-described permeate stream comprising hydrogen and hydrogen chloride enters the isomerization reaction zone 130 via a line 162. In the isomerization reaction zone 130, normal butane isomerizes to isobutane in the presence of a chloride-containing catalyst, but the specific composition of the particular chloride-containing catalyst is not critical to the success of this invention. An isomerization reaction zone effluent comprising hydrogen, hydrogen chloride, light $C_1$ to $C_3$ hydrocarbons, isobutane, normal butane, and higher-boiling $C_4+$ hydrocarbons is withdrawn from the isomerization reaction zone 130 through a line 142. The isomerization reaction zone 130 may comprise reactor(s), heat exchanger(s), compressor(s), and other equipment which are conventional, are known to persons of ordinary skill in the art of hydrocarbon processing, and need not be described in detail herein. The particular locations within the isomerization reaction zone 130 to which the streams in the lines 101, 111, 126, and 162 pass and from which the effluent in the line 142 passes are not critical to the practice of this invention.

The isomerization reaction zone effluent passes through the line 142 to a stabilizer column 140. The stabilizer column 140 separates dissolved hydrogen, hydrogen chloride, and light $C_1$ to $C_3$ hydrocarbons from the effluent of the second isomerization reactor 130. The overhead vapor stream of the stabilizer column 140, which contains hydrogen, hydrogen chloride, and light $C_1$ to $C_3$ hydrocarbons, passes through a line 144 to a partial condenser 146. The effluent of the condenser 146 flows through a line 148 to a stabilizer overhead receiver 150. All of the condensed liquid that enters the stabilizer overhead receiver 150 is withdrawn through a line 152 and is returned to the stabilizer 140 as reflux. The vapor stream from the overhead receiver 150 contains hydrogen, hydrogen chloride, and light $C_1$ to $C_3$ hydrocarbons and passes through a line 154 to a membrane separation zone 160.

The function of the membrane separation zone 160 is to separate the hydrogen and hydrogen chloride from the light $C_1$ to $C_3$ hydrocarbons in the vapor stream flowing in the line 154. The membrane separation zone 160 contains a resin membrane 163 comprising a polymer or copolymer containing the polymer repeat unit of the previously mentioned formula (I). Most of the light hydrocarbons in the vapor stream from the overhead receiver 150 do not selectively pass through the membrane 163 but instead are withdrawn in a line 156 in a nonpermeate stream that can be burned as fuel. Most of the hydrogen and hydrogen chloride that is present in the vapor stream in the line 154 selectively passes through the membrane 163 and is recovered in the permeate stream, which exits the membrane separation zone 160 in the line 162. In order to improve the driving force for the selective passage of hydrogen and hydrogen chloride through the membrane 163, a sweep stream passes through a line 158 to the permeate side of the membrane 163. The sweep stream may be a vapor sidecut from a lower portion of the stabilizer column 140, but the sweep stream is preferably a liquid stream from the bottom of the stabilizer column 140 that is subsequently vaporized. In either case, the sweep stream is a vapor stream and has low mole fractions of hydrogen and hydrogen chloride, and therefore the sweep stream tends to dilute the partial pressures of hydrogen and hydrogen chloride on the permeate side of the membrane 163. The permeate stream in the line 162 thus contains not only hydrogen and hydrogen chloride that permeated through the membrane 163 but also components of the sweep stream.

Isobutane, normal butane, and higher-boiling $C_4+$ hydrocarbons are recovered from the bottom of the stabilizer column 140 in a bottoms stream that flows in a line 168. The bottoms stream is divided into four portions. A small portion of the bottoms stream serves as the previously-mentioned sweep stream and is routed via the line 158 through a vaporizer (not shown) to the membrane separation zone 160. The remaining part of the bottoms stream flows through a line 170, and a second portion flows through a line 178, is reboiled in reboiler 180, and recirculates to the stabilizer column 140 via a line 182. Another portion of the bottoms stream flows to storage through a line 172 and a line 173. The final portion of the bottoms stream flows through the line 172 and is recycled to the deisobutanizer zone 110 via the line 103, as described previously.

FIG. 3, as previously mentioned, is a preferred embodiment of this invention for use in pentane and hexane isomerization. Referring now to FIG. 3, a dried fresh charge stock which comprises normal pentane and normal hexane enters the process through a line 201 and passes into an isomerization reaction zone 230. Makeup hydrogen, also dried, enters the isomerization reaction zone 230 via a line 226, and a hereinafter-described permeate stream comprising hydrogen and hydrogen chloride enters the isomerization reaction zone 230 via a line 262. In the isomerization reaction zone 230, in the presence of a chloride-containing catalyst, normal pentane isomerizes to isopentane (2-methylbutane), and normal hexane isomerizes mainly to 2,2-dimethylbutane but also to 2-methylpentane, 3-methylpentane, and 2,3-dimethylbutane. The specific composition of the particular chloride-containing catalyst is not critical to the success of this invention. An isomerization reaction zone effluent comprising hydrogen, hydrogen chloride, light $C_1$ to $C_4$ hydrocarbons, normal pentane, isopentane, normal hexane, 2,2-dimethylbutane, 2,3-dimethylbutane, 2-methylpentane, 3-methylpentane, and higher-boiling $C_6+$ hydrocarbons is withdrawn from the isomerization reaction zone 230 through a line 242. The isomerization reaction zone 230 may comprise reactor(s), heat exchanger(s), compressor(s), and other equipment which are conventional, are known to persons of ordinary skill in the art of hydrocarbon processing, and need not be described in detail herein. The particular locations within the isomerization reaction zone 230 to which the streams in the lines 201, 226, and 262 pass, and from which the effluent in the line 242 passes, are not critical to the practice of this invention.

The isomerization reaction zone effluent passes through the line 242 to a stabilizer column 240. Stabilizer column 240 produces an overhead vapor stream comprising light $C_1$ to $C_4$ hydrocarbons, hydrogen, and hydrogen chloride that flows through a line 244. The overhead vapor stream passes through a line 244 to a partial condenser 246. The partially condensed overhead stream flows through a line 248 and enters an overhead receiver 250. All of the condensed liquid entering the overhead receiver 250 returns to the stabilizer column as reflux via a line 252. The vapor stream from the overhead receiver 250, which contains hydrogen chloride, hydrogen, and light $C_1$ to $C_4$ hydrocarbons, passes through a line 254 to a membrane separation zone 260.

Membrane separation zone 260 contains a resin membrane 263 comprising a polymer or copolymer containing the polymer repeat unit of the previously mentioned formula (I). Most of the light hydrocarbons flowing in line 254 are recovered in the nonpermeate stream flowing in a line 256. Most of the hydrogen and hydrogen chloride flowing in the line 254 selectively passes through the membrane 263 and are recovered in the permeate stream in a line 262. A sweep stream passes through a line 258 to the permeate side of the membrane 263. Although the sweep stream may be a vapor sidecut from the stabilizer column 240, the sweep stream is preferably a portion of the liquid bottoms stream of the stabilizer column 240 that is subsequently vaporized. The sweep stream contains less than 1 mol-% hydrogen and less than 0.01 mol-% (100 mol-ppm) hydrogen chloride in order to enhance the driving force for permeation through the membrane 263 of hydrogen and hydrogen chloride, as described previously.

The bottoms stream of the stabilizer column 240 contains mostly branched pentanes and branched hexanes that are recovered in a line 268. A small portion of the bottoms stream is the previously mentioned sweep stream that is routed via the line 258 to the membrane separation zone 260. The remaining part of the bottoms stream passes through a line 270. Another portion of the bottoms stream passes through a line 278, is reboiled in a reboiler 280, and returns to the stabilizer column 240 via a line 282. The final portion of the stabilizer bottoms stream is the net product, which flows through a line 272.

EXAMPLES

A membrane comprising a polymer or copolymer containing the polymer repeat unit of the previously mentioned formula (I) was tested for permeation of hydrogen chloride as follows. A feed comprising 5 mol-% hydrogen chloride, 10 mol-% hydrogen, 80 mol-% methane, and 5 mol-% propane was passed to a micromodule containing a 6F-SPS membrane obtained from Innovative Membrane Systems. The membrane was maintained at a constant temperature of 150° F. (66° C.) in a temperature controlled box. The feed passed to the permeate side of the micromodule, which was maintained at a pressure of 100 psi(a) (689.5 kPa(a)). Nonpermeate was withdrawn from the nonpermeate side of the membrane. Permeate was withdrawn from the permeate side of the membrane and a portion of the permeate was analyzed by a gas chromatograph. The permeate side of the micromodule was maintained at 15 psi(a) (103.4 kPa(a)). Rotometers measured the flow rates of the feed, nonpermeate, and permeate. The stage cut, which is defined as the volumetric flow rate of the permeate divided by the volumetric flow rate of the feed times 100, was from 1 to 3 percent. These conditions of the micromodule were maintained for 201 hours. The observed selectivities were as follows:

| Components | Selectivity |
|---|---|
| Methane relative to propane | 3–3.5 |
| Hydrogen relative to hydrogen chloride | 1.2–2.5 |
| Hydrogen chloride relative to methane | 60–90 |

These selectivities show the surprising results that hydrogen chloride permeates through the membrane from 60 to 90 times faster than methane, and even faster yet relative to propane. It is believed that hydrocarbons heavier than propane permeate through the membrane even more slowly than propane, and so hydrogen chloride permeates much faster than all of the light hydrocarbons. These data also show the unexpected result that the permeability of hydrogen chloride is almost as great as (i.e., 40 to 83%) of hydrogen, which is the component of the feed that permeates most readily through the membrane.

What is claimed is:

1. A process for the alkylation of an alkylation substrate with an alkylating agent, the process comprising the steps of:
    a) passing an alkylating agent and an alkylation substrate to an alkylation reaction zone, alkylating the alkylation substrate with the alkylating agent in the presence of a chloride-containing catalyst to form alkylate, and recovering from the alkylation reaction zone a reaction effluent stream comprising alkylate, hydrocarbons having from 1 to 7 carbon atoms, and hydrogen chloride;
    b) passing at least a portion of the reaction effluent stream to a product separation zone operating at conditions to separate the entering hydrocarbons, and withdrawing from the product separation zone a recycle stream comprising hydrocarbons having from 1 to 7 carbon atoms and hydrogen chloride;
    c) passing at least a portion of the recycle stream to a membrane separation zone comprising a resin membrane comprising a polymer or copolymer containing the polymer repeat unit represented by the formula,

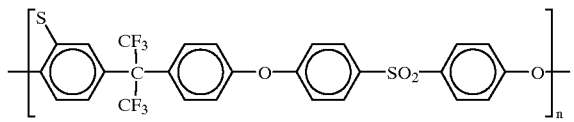

wherein S is the sulfonic acid group or its salified form and wherein n represents the average number of polymer repeat units in the polymer or copolymer and wherein the polymer or copolymer has a molecular weight above about 10,000 and a degree of substitution of S groups of from about 0.2 to about 4;
    d) withdrawing from the membrane separation zone a permeate comprising hydrogen chloride; and
    e) recovering alkylate from the process.

2. The process of claim 1 further characterized in that at least a portion of the permeate stream is recycled to the alkylation reaction zone.

3. The process of claim 1 further characterized in that a nonpermeate stream having a first mole fraction of hydrogen chloride is recovered from the nonpermeate side of the resin membrane, the nonpermeate side operates at a nonpermeate pressure, the permeate side of the resin membrane operates at a permeate pressure, a sweep stream having a second mole fraction of hydrogen chloride is introduced to the permeate side, and the product of the second mole fraction and the permeate pressure is not greater than the product of the first mole fraction and the nonpermeate pressure.

4. The process of claim 1 wherein the alkylation substrate is a paraffin and the alkylating agent is an olefin.

5. A process for the alkylation of a $C_4$–$C_5$ branched paraffin with a $C_3$–$C_5$ olefin, the process comprising the steps of:

a) passing $C_3$–$C_5$ olefins, a first recycle stream comprising $C_4$–$C_5$ branched paraffins, and a second recycle stream comprising $C_4$–$C_5$ branched paraffins and hydrogen chloride to an alkylation reaction zone, alkylating $C_4$–$C_5$ branched paraffins with $C_3$–$C_5$ olefins in the presence of a catalyst containing chloride to form alkylate and depositing heavy hydrocarbons on the catalyst in the alkylation reaction zone, and recovering from the alkylation reaction zone a reaction effluent stream comprising alkylate, $C_4$–$C_5$ branched paraffins, $C_1$–$C_3$ hydrocarbons, hydrogen chloride, and catalyst containing heavy hydrocarbon deposits;

b) passing at least a portion of the reaction effluent stream to a product separation zone operating at conditions to separate the entering hydrocarbons and catalyst, withdrawing from the product separation zone a product separation zone effluent stream comprising alkylate, $C_4$–$C_5$ branched paraffins, $C_1$–$C_3$ hydrocarbons, and hydrogen chloride, and withdrawing from the product separation zone catalyst having heavy hydrocarbons deposited thereon;

c) passing catalyst withdrawn from the product separation zone to a regeneration zone, the regeneration zone operating at regeneration conditions sufficient to remove at least a portion of the heavy hydrocarbons from the catalyst in the regeneration zone, withdrawing from the regeneration zone at least partially regenerated catalyst containing less heavy hydrocarbon deposits than the catalyst passed to the regeneration zone, and recycling at least partially regenerated catalyst to the alkylation reaction zone;

d) passing a paraffin makeup stream comprising $C_4$–$C_5$ branched paraffins and at least a portion of the product separation zone effluent stream to a branched paraffin separation zone, and withdrawing from the branched paraffin separation zone a gaseous branched paraffin separation zone overhead stream comprising $C_1$–$C_3$ hydrocarbons and hydrogen chloride, a gaseous sweep stream comprising $C_4$–$C_5$ branched paraffins and having a first mole fraction of hydrogen chloride, the first recycle stream, and a branched paraffin separation zone bottom stream comprising alkylate;

e) passing the branched paraffin separation zone overhead stream to a membrane separation zone comprising a resin membrane comprising a polymer or copolymer containing the polymer repeat unit represented by the formula,

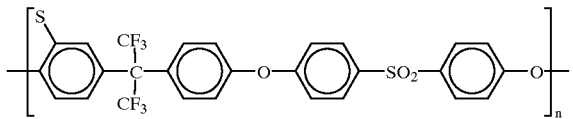

wherein S is the sulfonic acid group or its salified form and wherein n represents the average number of polymer repeat units in the polymer or copolymer and wherein the polymer or copolymer has a molecular weight above about 10,000 and a degree of substitution of S groups of from about 0.2 to about 4, the nonpermeate side of the resin membrane operating at a nonpermeate pressure, and the permeate side of the resin membrane operating at a permeate pressure;

f) passing the sweep stream to the permeate side of the resin membrane;

g) recovering a nonpermeate stream comprising $C_1$–$C_3$ hydrocarbons and having a second mole fraction of hydrogen chloride from the nonpermeate side of the resin membrane, the product of the first mole fraction and the permeate pressure being not greater than the product of the second mole fraction and the nonpermeate pressure, and rejecting the nonpermeate stream from the process;

h) recovering a permeate stream comprising $C_4$–$C_5$ branched paraffins and hydrogen chloride from the permeate side of the resin membrane, and withdrawing the permeate stream from the membrane separation zone; and i) forming the second recycle stream from at least a portion of the permeate stream.

6. The process of claim 1 further characterized in that the paraffin makeup stream comprises $C_4$–$C_5$ normal paraffins, a reject stream comprising $C_3$ hydrocarbons and $C_4$–$C_5$ normal paraffins is withdrawn from the branched paraffin separation zone, and the reject stream is rejected from the process.

7. The process of claim 1 further characterized in that the branched paraffin separation zone overhead stream comprises hydrogen and the permeate stream contains at least a portion of the hydrogen in the branched paraffin separation zone overhead stream.

* * * * *